US009342495B2

(12) United States Patent  (10) Patent No.: US 9,342,495 B2
Kimber et al.  (45) Date of Patent: May 17, 2016

(54) METHODS, SOFTWARE AND DEVICES FOR IMPROVING VISIBILITY OF USER-FILLED DATA IN AN ELECTRONIC FORM

(75) Inventors: Ryan Kimber, Toronto (CA); Tommy Trinh, Toronto (CA); Alfred Wong, Toronto (CA)

(73) Assignee: THINK RESEARCH CORPORATION, Toronto (CA)

( * ) Notice: Subject to any disclaimer, the term of this patent is extended or adjusted under 35 U.S.C. 154(b) by 607 days.

(21) Appl. No.: 13/552,061

(22) Filed: Jul. 18, 2012

(65) Prior Publication Data

US 2014/0026024 A1 Jan. 23, 2014

(51) Int. Cl.
 G06F 17/00 (2006.01)
 G06F 17/24 (2006.01)
 G06F 19/00 (2011.01)

(52) U.S. Cl.
 CPC ............ *G06F 17/243* (2013.01); *G06F 19/322* (2013.01); *G06F 19/363* (2013.01)

(58) Field of Classification Search
 CPC .................................................. G06F 17/243
 See application file for complete search history.

(56) References Cited

U.S. PATENT DOCUMENTS

| 2002/0023108 A1* | 2/2002 | Daswani ............... G06F 17/243 715/224 |
| 2004/0034831 A1* | 2/2004 | Grober et al. ................. 715/507 |
| 2004/0181749 A1* | 9/2004 | Chellapilla ........... G06F 17/243 715/222 |
| 2005/0055438 A1* | 3/2005 | Matti ......................... 715/501.1 |
| 2007/0209015 A1* | 9/2007 | Ritter .................... G06F 3/0237 715/780 |
| 2008/0184102 A1* | 7/2008 | Selig ..................... G06F 17/243 715/234 |
| 2011/0131479 A1* | 6/2011 | Padgett et al. ................ 715/223 |
| 2013/0238965 A1* | 9/2013 | Barrus .......................... 715/223 |

* cited by examiner

*Primary Examiner* — Keith Bloomquist

(57) ABSTRACT

Methods, software, and devices for processing a user-filled form are disclosed. A parsable electronic representation of the user-filled form is received. Based on parsing this electronic representation, at least one of a first or a second subset of input elements is identified. The first subset of input elements represents input fields that have received user-filled data while the second subset of input elements represents input fields that have not received user-filled data. Those text elements representing text providing descriptive context to input fields represented by the identified subset of input elements are associated with the identified subset of input elements. A graphical representation of the user-filled form is generated. In this graphical representation, text represented by text elements associated the first subset of input elements are highlighted relative to text represented by text elements associated with the second subset of input elements.

19 Claims, 7 Drawing Sheets

```
<contentBlock x="54.72" x2="282.35" y="468.72" y2="483.6"
stringRepresentation="[CBX] Pharmacist – Reason: [TXT]"/>

<checkboxField x="54.72" x2="64.68" y="468.72" y2="478.67" disabled="false" visible="true" key="'1m-
aQEu6vq0IH8AAQGqdw[0]" qualityIndicator="false" />

<textElement x="68.05" x2="79.69" y="470.23" y2="480.19" stringRepresentation="Pharmacist" />

<textElement x="82.33" x2="85.66" y="470.23" y2="480.19" stringRepresentation="-" />
<textElement x="88.09" x2="117.44" y="470.23" y2="480.19" stringRepresentation="Reason:" />

<textField x="127.19" x2="282.35" y="469.2" y2="483.6" disabled="false" visible="true" key="'1m-
aQEu6vq0IH8AAQGqdw[1]" qualityIndicator="false" />

</contentBlock>
```

FIG. 4

☐ Pharmacist – Reason: _____

FIG. 6

(e.g. HIV, immunocompromised or cystic fibrosis)
☐ Pharmacist – Reason: _____  ☐ SLP – Reason: _____
☑ PT – Reason: Chest Physiotherapy        (e.g. if aspiration pneumonia)
Other: _____                    ☐ SW – Reason: _____
                                          Reason: _____

Diet
☐ NPO, medications with sips
☐ NPO, no PO medications until assessment by SLP in a.m.

FIG. 7

Patient Order Sets.com

Document alleries on organization approved form

Patient name: John Doe
Patient address: 123 Main St.
Toronto, ON
Visit #: 12345

Community Acquired Pneumonia Admission Order Set

*Ensure Medication Reconcilliation Form has been reviewed*

| | Action |
|---|---|

Admit to ____ICU____ Dr. ____Jones____ _____ to consult/assume MRP

Diagnosis Community Acquired Pneumonia ☑ Bacterial Pneumonia

Precautions: ☑ Contact ☑ Droplet ☐ Airborne – Reason: _____ Risk of infection

Code Status: ☑ Full Resuscitation or _____

Family Physician: ____Dr. Smith____

Consults

☐ Dietitian – Reason: _____    ☑ Respirologist – Reason: _____

☐ Infectious Diseases MD – Reason: _____    ☐ RRT – Reason: teach puffer use
(e.g. HIV, immunocompromised or cystic fibrosis)

☐ Pharmacist – Reason: _____    ☐ SLP – Reason: _____
(e.g. if aspiration pneumonia)

☑ PT – Reason: Chest Physiotherapy    ☐ SW – Reason: _____

☐ Other: _____    Reason: _____

Diet

☐ NPO, medications with sips    ☐ NPO, no PO medications until assessment by SLP in a.m.

FIG. 8

METHODS, SOFTWARE AND DEVICES FOR IMPROVING VISIBILITY OF USER-FILLED DATA IN AN ELECTRONIC FORM

FIELD OF THE INVENTION

The present invention relates to processing electronic documents, particularly to methods, software, and devices for improving visibility of user-filled data in an electronic form.

BACKGROUND OF THE INVENTION

Forms are commonly used to gather information. They are used in a myriad of applications, e.g., when filing tax returns, when making an online purchase using a credit card, when answering a questionnaire, etc. Forms simplify the process of providing information because forms may present users with instructions on what information should be provided in the appropriate spaces, and may also present users with a multitude of options from which they can conveniently select, for example, as a series of checkboxes. In recent years, with the proliferation of computers, electronic documents and Internet use, use of electronic forms has become wide-spread.

However, while forms, including electronic forms, make it easier for users to provide information, they present certain problems for those who read user-filled forms. User-filled forms often present information very densely to readers. Selected options are presented amongst unselected options. Filled sections of the form are presented along with unfilled sections of the form that may not be applicable to the particular user who filled the form. Readers are confronted with the problem of scanning the form to locate user-filled data. This problem may be especially difficult when readers deal with electronic forms, as user-filled data is not hand-written, and thus cannot be distinguished from printed form text on that basis. To the contrary, in an electronic form, user-filled data and form text may be presented to the reader in the same print, font face, etc. Readers may thus miss user-filled data when reading the form. These problems may be particularly severe when electronic forms are used in a hospital, a setting in which successful medical treatment routinely depends on user-filled data being read completely and accurately.

In a hospital, patients receive treatments (blood tests, medications, diagnostic tests, procedures, etc.) by way of a practitioner's orders carried out by hospital staff. Historically, those orders were hand-written by the practitioner.

Hand-writing orders requires the practitioner to remember all of the appropriate tests, medications and treatment options, the right sequence of steps, the right drug among many similarly named options, and to write legibly. This is a challenging task because each patient typically has many conditions that need to be addressed, there are thousands of medical conditions the doctor must remember, and patients can often need many orders to receive all the care required. Furthermore, modern medical knowledge is constantly evolving.

Many hospitals now use order sets instead of hand-written orders. Order sets are pre-defined forms that specify all the up-to-date treatment options, in a standardized format, from which the practitioner may select. For any given diagnosis, a form exists that provides predefined treatment checklists, allowing the practitioner to simply select the treatments being ordered for the patient. The form may also allow the practitioner to enter textual instructions for more clarity, as needed. Order sets may be generated in or converted to electronic format, which can then be printed out in hard copy or provided electronically to hospital staff for execution.

One drawback of order sets, however, is that information is presented very densely to hospital staff. This density arises in part because a completed order set contains both selected and unselected treatment options, form text providing descriptive content to those treatment options, as well as any textual instructions entered by the practitioner. The inclusion of unselected treatment options provides valuable context for hospital staff and other practitioners, but their presence may cause hospital staff to miss selected treatment options and textual instructions from the practitioner, thereby creating risk to patient safety.

Accordingly, there is a need for methods and software for improving visibility of user-filled data in an electronic form.

SUMMARY OF THE INVENTION

In accordance with an aspect of the present invention, there is provided a method of processing a user-filled form, the method comprising: receiving a parsable electronic representation of the user-filled form, the electronic representation comprising: a plurality of input elements, each of the plurality of input elements representing an input field in the user-filled form, the input field for receiving user-filled data; a plurality text elements, each of the plurality of text elements representing text in the user-filled form, the text providing descriptive context to an input field; a plurality of data elements, each of the plurality of data elements representing user-filled data in the user-filled form, received in an input field; parsing the electronic representation, and based on the parsing: identifying at least one subset of input elements of the plurality of input elements among: a first subset of input elements of the plurality of input elements, the first subset of input elements representing input fields that have received user-filled data represented by the plurality of data elements; or a second subset of input elements of the plurality of input elements, the second subset of input elements representing input fields that have not received user-filled data; associating with the at least one subset of input elements those text elements of the plurality of text elements representing text providing descriptive context to input fields represented by the at least one subset of input elements; generating a graphical representation of the user-filled form based on the plurality of input elements, the plurality of text elements and the plurality of data elements, with text represented by text elements associated the first subset of input elements highlighted relative to text represented by text elements associated with the second subset of input elements.

In accordance with another aspect of the present invention, there is provided a computing device for processing a user-filled form, the computer device comprising: a processor; memory in communication with the processor; and software code stored in the memory, executable on the processor, the software code comprising: a receiving module to receive a parsable electronic representation of the user-filled form, the electronic representation comprising: a plurality of input elements, each of the plurality of input elements representing an input field in the user-filled form, the input field for receiving user-filled data; a plurality text elements, each of the plurality of text elements representing text in the user-filled form, the text providing descriptive context to an input field; a plurality of data elements, each of the plurality of data elements representing user-filled data in the user-filled form, received in an input field; a parsing module to parse the electronic representation; an identifying module to identify at least one subset of input elements of the plurality of input elements among: a first subset of input elements of the plurality of input elements, the first subset of input elements representing input fields that have received user-filled data represented by the plurality of data elements; or a second subset of input elements of the plurality of input elements, the second subset of input elements representing input fields that have not received user-filled data; an associating module to associate with the at least one subset of input elements those text elements of the plurality of text elements representing text providing descriptive context to input fields represented by the at least one subset of input elements; a generating module to generating a graphical representation of the user-filled form based on the plurality of input elements, the plurality of text elements and the plurality of data elements, with text represented by text elements associated the first subset of input elements highlighted relative to text represented by text elements associated with the second subset of input elements.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate by way of example only, embodiments of this invention:

FIG. 4 illustrates an excerpted portion of an example XML document produced by the parsing module of the form processing software of FIG. 3.

FIG. 6 illustrates a further excerpted portion of the example order set form of FIG. 5 corresponding to one order option.

FIG. 7 illustrates a region corresponding to the order option of FIG. 6 being visually masked.

FIG. 8 illustrates a graphical representation of the portion of the example order set form of FIG. 5, after processing to improve visibility of user-filled data.

DETAILED DESCRIPTION

Figure 1:
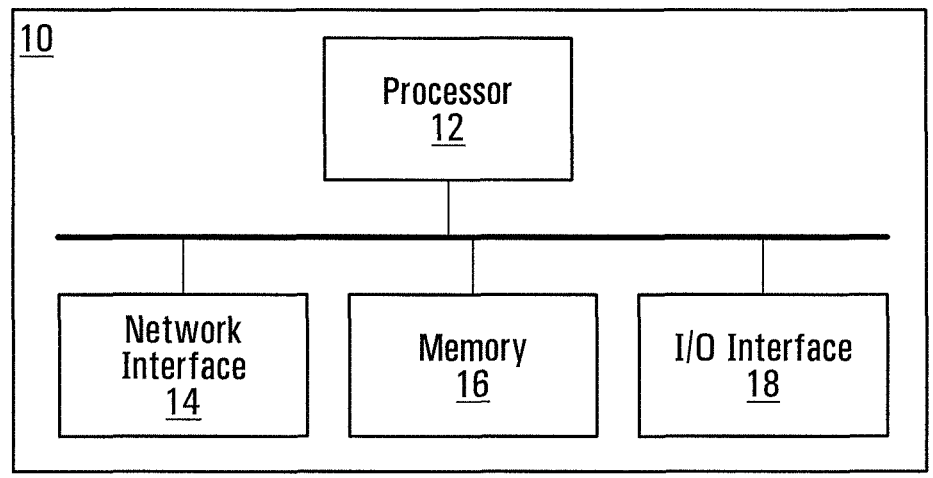
FIG. 1 is a high level block diagram of a computer device for use as a form processing server, exemplary of an embodiment of the present invention.

FIG. 1 is a high-level block diagram of computing device 10 operating as a form processing server, exemplary of the present invention. As will be come apparent, computing device 10 includes software for processing electronic forms to improve visibility of user-filled data in manners exemplary of the present invention.

As illustrated, computing device 10 includes processor 12, network interface 14, a suitable combination of persistent storage memory 16, random access memory and read only memory, and I/O interface 18. Processor 12 may be an Intel x86, PowerPC, ARM processor or the like. Network interface 14 interconnects computing device 10 to a data network such a private local area packet-switched data network or the public Internet. Additional input/output peripherals such as keyboard, monitor, mouse, scanner, printer and the like of computing device 10 are not specifically detailed herein. Computing device 10 may also include peripheral devices usable to load software exemplary of the present invention into its memory from a computer-readable medium. Peripheral devices may be interconnected to computing device 10 by one or more I/O interfaces 18. Computing device 10 may execute this software to adapt it to operate as a form processing server in manners exemplary of the present invention.

Figure 2:
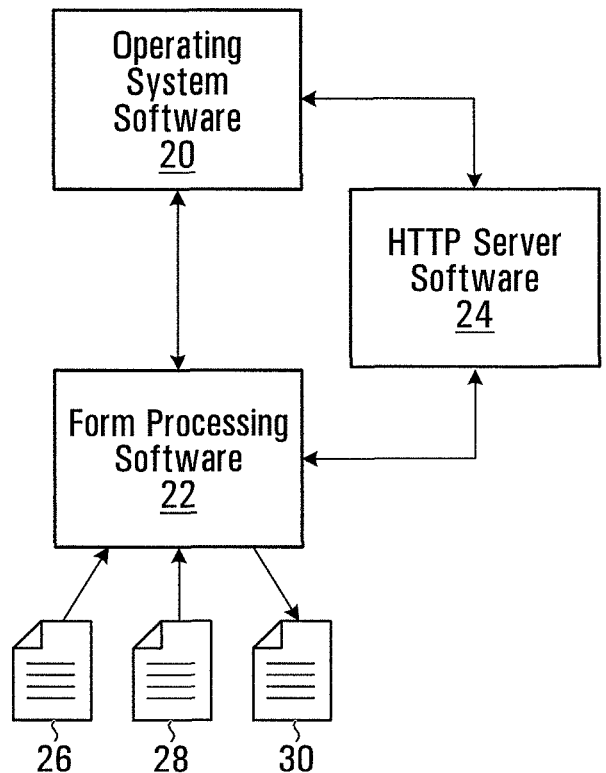
FIG. 2 illustrates the software organization of a form processing server, exemplary of an embodiment of the present invention.

FIG. 2 depicts a simplified organization of this software for storage and execution at computing device 10, exemplary of an embodiment of the present invention. As illustrated, this software includes operating system (O/S) software 20, form processing software 22, and HTTP server software 24.

Form processing software 22, in combination with O/S software 20 and HTTP server software 24, adapts computing device 10 to operate as a form processing server to process a user-filled electronic form and to generate a graphical representation of the form in which visibility of user-filled data is improved, exemplary of embodiments of the present invention.

A user-filled electronic form is represented by a combination of form template 26 and user-filled data 28. Form template 26 is an electronic representation of the structural elements of the form, including input elements and text elements. Each input element represents an input field in the form. User-filled data is received in input fields, e.g., text input fields, date input fields, numerical input fields, checkboxes, radio selection boxes, drop-down selection boxes, multiple-choice boxes, etc. Each text element represents text such as words or characters in the form which provide descriptive context to an associated input field.

User-filled data 28 includes data elements, where each data element represents a piece of data filled by the user, e.g., a checkbox selection, textual instructions filled into a text input field, a number filled into a numerical input field, a selection for a drop-down selection box, etc.

One or both of form template 26 and user-filled data 28 may be stored in a parsable form, for example, in memory 16 of computing device 10. This parsable form may be an electronic document in Portable Document Format (PDF), Rich Text Format (RTF), Extensible Markup Language (XML), HyperText Markup Language (HTML) or the like. This parsable form may also be an electronic message, such as an HTTP message. In some embodiments, form template 26 may simply be a blank version of the electronic form filled by the user.

Form processing software 22 processes form template 26 and user-filled data 28 to generate graphical representation 30 of the user-filled electronic form in which visibility of user-filled data is improved, exemplary of embodiments of the present invention.

O/S software 20 may, for example, be a Unix-based operating system (e.g., Linux, FreeBSD, Solaris, OSX, etc.), a Microsoft Windows operating system or the like. O/S software 20 allows form processing software 22 to access processor 12, network interface 14, memory 16 and one or more I/O interfaces 18 of computing device 10. O/S system software 20 may include a TCP/IP stack allowing computing device 10 to communicate with interconnected computing devices through network interface 14 using the TCP/IP protocol.

HTTP server software 24 is a conventional HTTP web server application such as the Apache HTTP Server, nginx, Microsoft IIS or similar server application. HTTP server software 24 allows computing device 10 to act as a conventional HTTP server and provides a plurality of documents for access according to TCP/IP protocol by network-interconnected computing devices operated by users. Documents may include web pages and blank forms. Web pages may be implemented using traditional web languages such as HTML, XHTML, Java, Javascript, Ruby, Python, Perl, PHP, Flash or the like. Blank forms may be provided in any fillable format, e.g., as HTML forms or PDF forms. HTTP server software 24 may also receive user-filled data 28, for example, when a user submits a completed form. HTML server software provides user-filled data 28 to form processing software 22 when submitted by the user.

Form processing software 22 includes a number of software modules, further detailed below. These modules of form processing software 22 may be written, for example, using conventional programming languages such as Java, J#, C, C++, C#, Perl, Visual Basic, Ruby, Scala, etc. These modules may additionally be written to use conventional web application frameworks such as the Java Servlet framework or the .NET Framework. Thus, the modules of form processing software 22 may be in the form of one or more executable programs, scripts, routines, statically/dynamically linkable libraries, or servlets.

In embodiments in which one or more modules of form processing software 22 are in the form of servlets, HTTP server software 24 may communicate with an interconnected servlet server application (not shown) such Apache Tomcat, IBM WebSphere, Red Hat JBoss, or the like. The servlet server application executes servlets on behalf of HTTP server software 24 to extend the ability of HTTP server software 24 to respond to HTTP requests, such as a request to process a user-filled electronic form.

Figure 3:
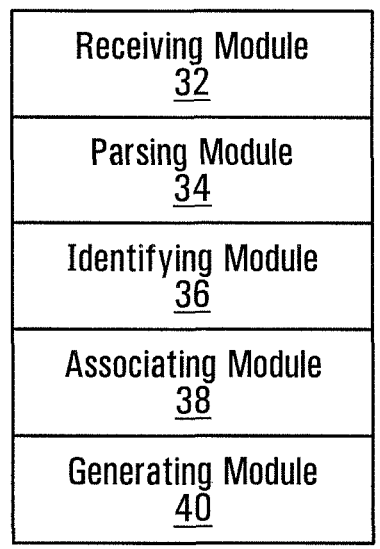
FIG. 3 is a high level block diagram of the modules of the form processing software of FIG. 2 executing on the form processing server of FIG. 1.

In the embodiment shown in FIG. 3, form processing software 22 includes a receiving module 32, parsing module 34, identifying module 36, associating module 38, and generating module 40. The functions of each module are detailed below.

Receiving module 32 receives form template 26 for processing by form processing software 22. Receiving module 32 may receive form template 26 from memory 16, or from a computer-readable medium connected to an I/O interface 18, or through network interface 14, e.g., by way of HTTP server software 24.

Parsing module 34 includes one or more parsers for parsing form template 26 to determine the structure of the user-filled electronic form. For example, parsing module may include an input field parser and a text parser.

An input field parser may be used to identify input elements which represent input fields in the user-filled electronic form. Input fields include, for example, text input fields for receiving textual data from users or checkbox fields which can be selected (checked) by users. This input field parser may also be used to determine the properties of input fields represented by identified input elements, as detailed below.

Each identified input element is assigned a unique FIELD_ID. As detailed below, this FIELD_ID is subsequently referenced in user-filled data 28 to identify the input element representing a particular input field that have been filled with data, where the data is represented by a data element in user-filled data 28.

A text parser may be used to identify text elements representing text in the user-filled form, such as individual characters or words (hereinafter referred to collectively as "words") in the user-filled electronic form. Words may provide descriptive context to an associated input field. Words are not limited to letters or dictionary words, but may include, for example, numbers or any Unicode character. This text parser may also be used to identify the properties of words represented by identified text elements, as detailed below.

In some embodiments, a single parser may perform the functions of both an input field parser and a text parser. For example, when form template 26 is a PDF document, PDFBox, distributed by the Apache Software Foundation, may be used as the input field parser and/or as the text parser.

Parsing module 34 of form processing software 24 creates a new PageElement object to correspond to each element identified by parsing form template 26. The PageElement class is a parent class to a number of subclasses including TextField, CheckboxField, and TextElement. The particular subclass of each PageElement object created depends on the type of element identified. For example, each TextField object or CheckboxField object is created to correspond to an identified input element representing a text input field or a checkbox field, respectively. Similarly, a TextElement object is created to correspond to an identified text element representing one or more words. PageElement objects of other subclasses may be created to correspond to other types of elements identified by parsing form template 26, such as radio buttons, images, hyperlinks, etc.

Each PageElement object contains the parsed properties of the corresponding element, such as x and y coordinates defining the location of the element on a page of form template 26. Other parsed properties may include font properties such as typeface, size or weight. Each PageElement object corresponding to an input element also contains the FIELD_ID assigned to that input element.

Parsing module 34 creates an UnstructuredDocument object to contain one or more Page objects, wherein each Page object represents one page of form template 26, and each Page object contains multiple PageElement objects.

Associating module 38 creates a StructuredDocument object corresponding to the UnstructuredDocument object. The StructureDocument object contains the PageElement objects of an UnstructuredDocument object, in which associated PageElement objects are grouped.

Like the UnstructuredDocument object, the StructuredDocument object contains Page objects. Each Page object in turn may contain Section objects and/or ContentBlock objects. Each Section object corresponds to a section of a page of form template 26 such as the header, footer, body, left margin, right margin, etc., and contains PageElement objects, each corresponding to an element within that section. PageElement objects are grouped into Section objects based on their location on a page, as identified for example based on parsed x and y coordinates for each PageElement object.

Each ContentBlock object is a further grouping of multiple PageElement objects, in which the group corresponds to a phrase, sentence, title, order option, etc. An order option may for example be a text input field and adjacent words providing descriptive context to that text input field, and/or a checkbox field and adjacent words providing descriptive context to that checkbox field.

Associating module 38 groups associated PageElement objects into ContentBlock objects. Different forms of associations are defined. For example, where words provide descriptive context to a checkbox, the text element representing those words is defined to be associated with the input element representing that checkbox. As a further example, where two words form a phrase or a sentence, the text elements respectively representing those two words are defined to be associated with each other.

Grouping is performed using the parsed properties of the PageElement objects, a set of Structure Rules and a business rule management system (BRMS) with a rules engine, such as JBoss Drools, ILOG JRules, FICO Blaze Advisor, or the like. The set of Structural Rules may include some or all of the following rules:

1) Combine a line starting with a TextElement with a TextField beside it.

2) Combine a line starting with a TextElement with a TextElement beside it.

3) Combine a line starting with a CheckboxField with a TextElement.

4) Combine a ContentBlock containing a Checkbox with a ContentBlock below containing only a TextField.

5) Combine a ContentBlock with a TextElement to the right.

6) Combine a ContentBlock with a TextField to the right.

7) Combine TextElements Far From Previous ContentBlocks.

8) Combine a TextField with a PageElement to the right where a ContentBlock to the left has Larger font.

9) Combine a ContentBlock alone on a line with another ContentBlock alone on a line below if both are only include TextElements.

10) Convert a TextElement alone on a line into a ContentBlock.

11) Convert a TextField alone on a line to ContentBlock.

By applying the set of Structural Rules to the PageElement objects in an UnstructuredDocument object, associated PageElement objects are grouped into respective ContentBlock objects of a StructuredDocument object.

As user-filled electronic forms filled from the same blank form have the same structure, it is unnecessary to parse form template 26 for each instance of a user-filled electronic form. After form template 26 corresponding to a particular blank form has been parsed to construct a StructuredDocument object, the StructuredDocument object may be stored for repeated use. Thereafter, whenever form processing software 22 processes a user-filled electronic form for which a StructuredDocument object has previously been created and stored, parsing module 34 may use the stored StructuredDocument object instead of parsing form template 26 to create the StructuredDocument object.

A StructuredDocument object may be stored in memory 16, for example in the form of an XML document. FIG. 4 shows an excerpted portion of an XML document representing one ContentBlock object of an example StructuredDocument object.

As shown in FIG. 4, the ContentBlock is stored as a contentBlock tag (corresponding to a ContentBlock object) enclosing a checkboxField tag (corresponding to a CheckBoxField object), three textElement tags (corresponding to three TextElement objects), and a textField tag (corresponding to a TextField object). Using these tags, the XML document describes the ContentBlock object in a StructuredDocument object to contain a CheckBox object, three TextElement objects and a TextField object. The XML document thus describes associations between input elements and text elements, i.e., the input elements representing the checkbox and the text input field are defined to be associated with the three text elements.

As also shown in FIG. 4, each XML tag also includes x and y coordinates defining the location of the corresponding object. These coordinates can be subsequently parsed and used to generate graphical representation 30 of the user-filled electronic form and to alter the visual appearance of the form, as detailed below. Each XML tag corresponding to an input element object (e.g., a TextField object or a CheckBoxField object) also includes the unique FIELD_ID assigned to that object. As shown in FIG. 4, the checkboxField object has a FIELD_ID of 11m-aQEu6vq0lH8AAQGqdw[0], while the textField object has a FIELD_ID of 11m-aQEu6vq0lH8AAQGqdw[1].

In some embodiments, the XML document representing the StructuredDocument object need not be produced by parsing module 34. In these embodiments, this XML document may be produced manually by an administrator or automatically using other software. The XML document may be produced at the time the electronic form is designed. In other embodiments, the document representing the StructuredDocument object may be stored in another format suitable for parsing, such as HTML/XHTML.

Receiving module 32 receives user-filled data 28, corresponding to an electronic form filled by a user for processing by form processing software 22. Receiving module 32 may receive user-filled data 28 from memory 16, or from a computer-readable medium connected to an I/O interface 18, or through network interface 14, e.g., by way of HTTP server software 24.

After users fill data into a form, e.g., a PDF form or an HTML form, as provided by the form processing server by way of HTTP server software 24, users may submit user-filled data 28 to the form processing server by way of an HTTP message such as a POST or GET request.

User-filled data 28 includes data filled by users and identifies the particular input elements representing input fields in the electronic form in which data were received. For example, user-filled data 28 may be a list of FIELD_ID and VALUE pairs, such as:

$$FIELD\_ID\_0 = VALUE\_0$$
$$FIELD\_ID\_1 = VALUE\_1$$
$$FIELD\_ID\_2 = VALUE\_2$$
...

Each of FIELD_ID_0, FIELD_1, FIELD_2, etc., corresponds to a previously assigned unique identifier for an input element representing an input field. Each of VALUE_0, VALUE_1, VALUE_2, etc., corresponds to data filled in the respective input field. User-filled data 28 need only include FIELD_ID and VALUE pairs for those input fields have been filled by the user.

User-filled data 28 may, be in any parsable format, such as an HTTP message format, XML format, comma-delimited text format or the like.

Parsing module 34 parses user-filled data 28 to identify data elements representing data filled by the user, and also to identify those input elements representing input fields which have been filled with data. As discussed above, each of these input elements may be identified based on a FIELD_ID provided in user-filled data 28.

Form processing software 22 uses a StructuredDocument object and data elements of user-filled data 28, collectively representing a user-filled electronic form, to generate graphical representation 30 of the user-filled electronic form, wherein visibility of user-filled data is improved in manners exemplary of the present invention.

Visibility of user-filled data in graphical representation 30 is improved relative to the user-filled electronic form by altering the visual appearance of each region of graphical representation 30 corresponding to a ContentBlock object including no user-filled data.

Identifying module 36 identifies those ContentBlock objects within the StructuredDocument object containing no user-filled data. First, identifying module 36 identifies those PageElement objects representing input fields (e.g., text input fields or checkbox fields) in which a user has filled data based on the FIELD_ID/VALUE pairs parsed from user-filled data 28. Then, identifying module 36 identifies those ContentBlock objects containing no PageElement objects representing input fields in which a user has filled data.

Generating module 40 generates graphical representation 30 in any format suitable for graphically representing a form, such as PDF, HTML/XHTML or Word format. Graphical representation 30 may be generated to be printable and/or editable.

Generating module 40 generates graphical representation 30 to be substantially visually similar to the user-filled electronic form. Generating module 40 generates elements in graphical representation 30 based on PageElement objects in the StructuredDocument object and the parsed properties of those PageElement objects, e.g., x and y coordinates and font properties. Graphical module 40 then fills graphical representation 30 with data based on data elements parsed from user-data 28.

Generating module 40 then alters the visual appearance of graphical representation 30 to improve the visibility of user-filled data. In some embodiments, visibility of user-filled data may be improved by altering the visual appearance of regions of graphical representation 30 corresponding to ContentBlock objects containing no user-filled data. The visual appearance of such a region may be altered, for example, by applying a visual mask to the region. In particular, this visual mask may be applied by overlaying at least one semi-transparent white box over the text in the region to reduce the contrast of that text. This box may be located and sized based on the properties (e.g., x and y coordinates) of TextElement objects in that ContentBlock object such that the box covers the locations of those TextElement objects. The visual appearance of a region may also be altered, for example, by changing a visual style of the region, e.g., by changing the font face, size, weight, or colour for the text in the region, or the background colour of the region, etc. A person skilled in the art will readily appreciate other ways of altering the visual appearance of regions containing no user-filled data in order to improve the visibility of user-filled data in other regions.

By altering the visual appearance of the regions of graphical representation 30 corresponding to each ContentBlock object determined to include no user-filled data, text represented by text elements associated with input elements representing input fields that do contain user-filled data become highlighted relative to text represented by text elements associated with input elements representing input fields that do not contain user-filled data. Thus, for example in graphical representation 30, reader attention is drawn to selected order options, yet unselected order options, which can provide valuable contextual information to readers, are still present and legible.

Figure 9:
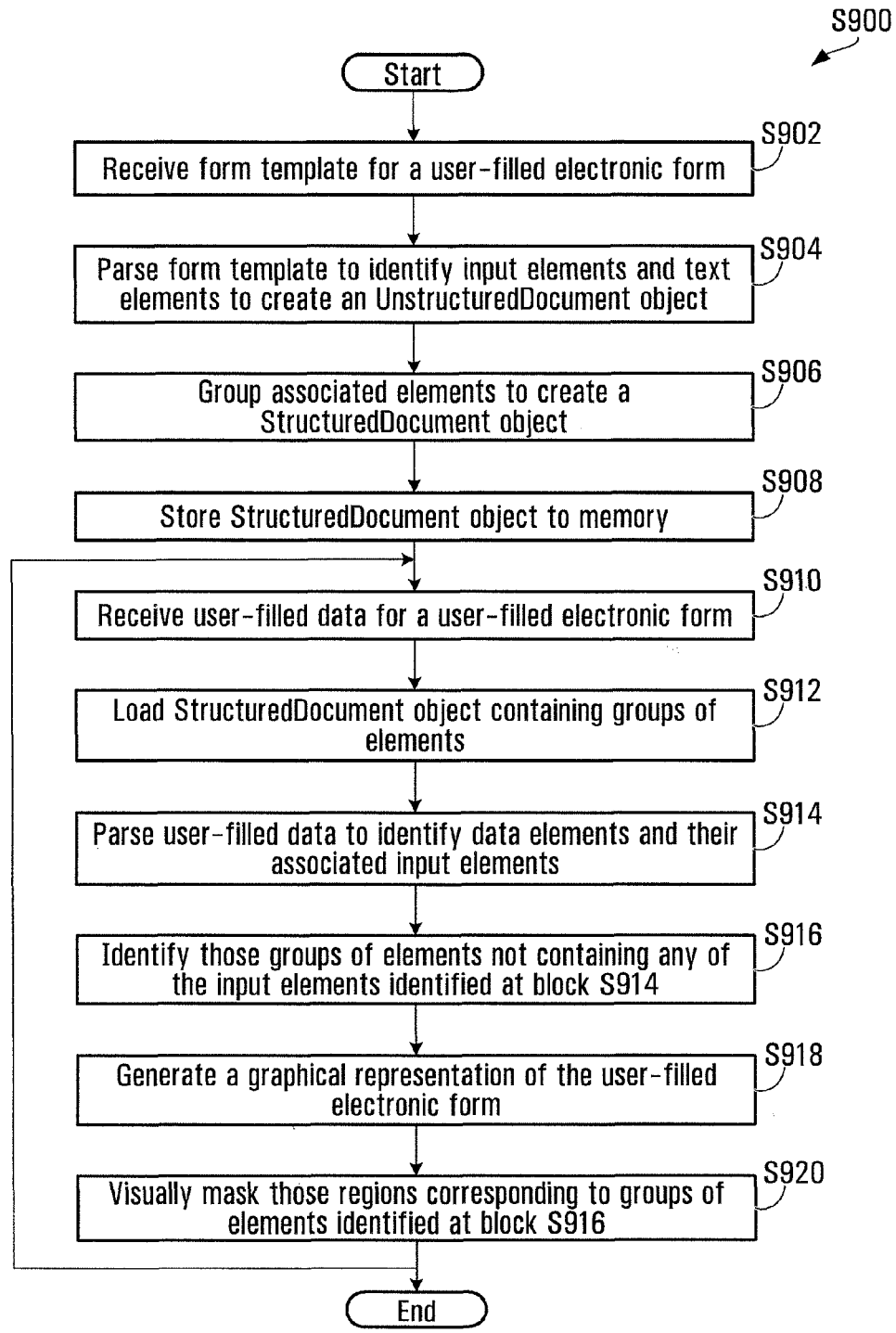
FIG. 9 is a flowchart illustrating exemplary blocks performed at the form processing server of FIG. 1.

The operation of form processing software 22 is further described with reference to an example order set form and FIG. 9, which illustrates the operation of a computing device under control of form processing software 22 in processing a user-filled form of FIGS. 5 and 6.

Figure 5:
FIG. 5 illustrates a portion of an example order set form that may be represented by the form template and the user-filled data of FIG. 2.

FIG. 5 depicts a portion of a user-filled order set form for treatment of Community Acquired Pneumonia. As illustrated, this order set form contains a number of selected order options and unselected order options, as well as textual instructions filled by a practitioner. For example, as illustrated, under the heading "Consults", the order options "PT" and "Respirologist" are selected, while the options "Dietician", "Infectious Diseases MD", "Pharmacist", "RRT", "SLP" and "SW" are unselected. For the selected order option "PT", the practitioner has also entered the textual instructions "Chest Physiotherapy".

In block S902, receiving module 32 of form processing software 22 receives form template 26 corresponding to the order set form depicted in FIG. 5. Upon receiving form template 26, at block S904 parsing module 34 parses form template 26 to identify the form's constituent input elements and text elements. Parsing module 34 creates a PageElement object to represent each parsed element.

FIG. 6 depicts an order option excerpted from the portion of the order set form depicted in FIG. 5. In this example order option, the words "Pharmacist—Reasons:" provide descriptive context to the adjacent checkbox field and the adjacent input text field. Form processing software 22 may parse this example order option of FIG. 6 into five PageElement objects, as follows:

a CheckboxField object corresponding to the checkbox,
a TextElement object corresponding to "Pharmacist",
a TextElement object corresponding to "-",
a TextElement object corresponding to "Reasons:"; and
a TextField object corresponding to the text input field.

Parsing module 34 creates a new Page object to contain these five PageElement objects and other PageElement objects corresponding to elements on the remainder of the form page. Parsing module 34 also creates an UnstructuredDocument object to contain this Page object.

Next, at block S906, associating module 38 creates a StructuredDocument object by applying a set of Structure Rules with a rules engine, as detailed above, to group PageElement objects into ContentBlock objects. For example, the five PageElement objects corresponding to order option as depicted in FIG. 6 are grouped into a single ContentBlock object. These ContentBlock objects are contained in a Page object, which in turn is contained in the StructuredDocument object. At block S908, the StructuredDocument object is stored in memory 16 as an XML document.

Subsequently, a user fills in an electronic form provided by form processing server by way of HTTP server software 24 and submits the filled data to the form processing server for processing. At block S910, receiving module 32 receives the filled data as user-filled data 28 in the form of an HTTP message. After user-filled data 28 is received by receiving module 32, at block S912 parsing module 34 recreates a StructuredDocument object by parsing the stored XML document corresponding to the electronic form filled by the user. As discussed above, this StructuredDocument objects contains ContentBlock objects, each of which contains associated PageElements objects. At block S914, parsing module 34 parses user-filled data 28 at identify data elements representing data filled by the user. Parsing module 24 also identifies associated input elements representing the input fields that have been filled with data.

Based on the identified input elements, at block S916, identifying module 36 then checks each ContentBlock object to identify all ContentBlock objects which do not contain any of those input elements, i.e., identify all ContentBlock objects which do not contain user-filled data, including the ContentBlock corresponding to the order option depicted in FIG. 4.

Generating module 40 then generates graphical representation 30 at block S918 to graphically represent the order set form depicted in FIG. 5. As detailed above, the graphical representation 30 is substantially visually alike to the user-filled electronic form, having the same text fields, input fields, and user-filled data.

As depicted in FIGS. 7 and 8, generating module 40 then visually masks text in regions corresponding to ContentBlock objects containing no user-filled data by forming a semi-transparent white box over the text at block S920. FIG. 7 shows the visual masking as applied to a sample region corresponding to the ContentBlock shown in FIG. 6. FIG. 7 depicts the size and location of the semi-transparent white box using dotted lines, and also depicts the resultant reduction in the contrast of text in the region covered by the box. FIG. 8 depicts graphical representation 30 corresponding to the portion of the user-filled electronic form shown in FIG. 5, after visual masking has been applied to each ContentBlock containing no user-filled data.

The above blocks S910 to S920 are repeated each time user-filled data 28 is received by form processing software 22, corresponding to a newly submitted user-filled electronic form.

In some embodiments, instead of altering the visual appearance of regions of graphical representation 30 corresponding to ContentBlock objects including no user-filled data, visibility of user-filled data may be improved by altering the visual appearance of regions of graphical representation 30 corresponding to ContentBlock objects including user-filled data. In these embodiments, identifying module 36 identifies those ContentBlock objects within the StructuredDocument object containing at least some user-filled data. Then, generating module 40 alters the visual appearance of regions of graphical representation 30 corresponding to these identified ContentBlock objects. The visual appearance of a region may be altered, for example, by overlaying a semi-transparent yellow box over the text to simulate yellow highlighting. The visual appearance of a region may also be altered, for example, by changing the visual style of the region, e.g., by bolding, underlining, italicizing, or otherwise emphasizing the text in the region, or by changing the font face, size, or colour, or by changing the background colour of the region, etc. A person skilled in the art will readily appreciate other ways of altering the visual appearance of regions with user-filled data in order to improve the visibility of that user-filled data.

In some embodiments, form processing software 22 need not create an XML document to store the StructuredDocument object, and therefore does not subsequently recreate the StructuredDocument object by parsing the XML document. In these embodiments, form processing software 22 may simply parse form template 26 to create a StructuredDocument each time that user-filled data 28 is received.

In alternate embodiments, form template 26 and user-filled data 28 may be received by form processing software 22 as a single document, or by way of a single HTTP message. For example, form processing software 22 may process a PDF document representing a user-filled form containing text elements, input elements and data elements. In these embodiments, form processing software 22 need not generate graphical representation 30, but rather may directly modify the received PDF document to improve visibility of user-filled data, in manners exemplary of the present invention.

A person skilled in the art will also appreciate that as generating module 40 only operates on a subset of ContentBlock objects, e.g., by visually masking regions corresponding to ContentBlock objects containing no user-filled data, or highlighting regions corresponding to ContentBlock objects containing user-filled data, it is not necessary for associating module 38 to form ContentBlock objects that do not belong in that subset. Therefore, in some embodiments, identifying module 36 may first identify those input elements representing input fields that have received data filled by the user, and then associating module 38 will only form ContentBlock objects including those identified input elements. Similarly, in other embodiments, identifying module 36 may first identify those input elements representing input fields that have not received data filled by the user, and then associating module 38 will only form ContentBlock objects including those identified input elements.

Of course, the above described embodiments are intended to be illustrative only and in no way limiting. The described embodiments of carrying out the invention are susceptible to many modifications of form, arrangement of parts, details and order of operation. For example, software (or components thereof) described at computing device 10 may be hosted at several devices. Software implemented in the modules described above could be using more or fewer modules. The invention, rather, is intended to encompass all such modification within its scope, as defined by the claims.

What is claimed is:

1. A method of processing a completed fillable form, said method comprising:

receiving a parsable electronic representation of said completed fillable form, said electronic representation comprising:
- a plurality of input elements, each of said plurality of input elements representing an input field in said completed fillable form, said input field for receiving user-filled data;
- a plurality of text elements, each of said plurality of text elements representing text in said completed fillable form, said text providing descriptive context to an input field;
- a plurality of data elements, each of said plurality of data elements representing user-filled data previously received from a user as input to an input field in said completed fillable form during completion of said fillable form by said user;

parsing said electronic representation, and based on said parsing:
identifying at least one subset of input elements of said plurality of input elements among:
- a first subset of input elements of said plurality of input elements, said first subset of input elements representing input fields that have received user-filled data represented by said plurality of data elements; or
- a second subset of input elements of said plurality of input elements, said second subset of input elements representing input fields that have not received user-filled data;

determining one or more groupings, each of said groupings associating at least one input element of said at least one subset of input elements with text elements of said plurality of text elements representing text providing descriptive context to input fields represented by said at least one input element;

generating a graphical representation of said completed finable form based on said plurality of input elements, said plurality of text elements and said plurality of data elements, wherein regions of said graphical representation corresponding to said one or more groupings are altered so as to improve visibility of portions of said graphical representation associated with said first subset of input elements relative to portions of said graphical representation associated with said second subset of input elements.

2. The method of claim 1, wherein said electronic representation is stored in the form of one or more electronic documents.

3. The method of claim 2, wherein at least one of said electronic documents is a Portable Document Format (PDF) document.

4. The method of claim 2, wherein at least one of said electronic documents is a Hypertext Markup Language (HTML) document.

5. The method of claim 2, wherein at least one of said electronic documents is an Extensible Markup Language (XML) document.

6. The method of claim 2, wherein said electronic representation is further stored in the form of one or more Hypertext Transfer Protocol (HTTP) messages.

7. The method of claim 6, wherein said one or more electronic documents represent said plurality of input elements and said plurality of text elements, and said one or more HTTP messages represent said plurality of data elements.

8. The method of claim 1, wherein said electronic representation further comprises pre-defined associations between said plurality of data elements and those input elements of said plurality of input elements representing input fields that have received user-filled data represented by said plurality of data elements.

9. The method of claim 8, wherein said parsing comprises identifying said pre-defined associations between said plurality of data elements and said those input elements of said plurality of input elements.

10. The method of claim 9, wherein said identifying at least one subset of input elements of said plurality of input elements is based at least on said pre-defined associations between said plurality of data elements and said plurality of input elements, as identified.

11. The method of claim 1, wherein said electronic representation further comprises pre-defined associations between said plurality of input elements and those text elements of said plurality of text elements representing text providing descriptive context to input fields represented by said plurality of input elements.

12. The method of claim 11, wherein said parsing comprises identifying said pre-defined associations between said plurality of input elements and said those text elements of said plurality of text elements.

13. The method of claim 12, wherein said associating is based at least on said pre-defined associations between said plurality of input elements and said those text elements of said plurality of text elements, as identified.

14. The method of claim 1, wherein said parsing comprises determining page coordinates for each input field represented by said at least one subset of input elements and for each text represented by said plurality of text elements.

15. The method of claim 14, wherein said associating is based at least on proximity of each input field represented by said at least one subset of input elements relative to text represented by said plurality of text elements, said proximity calculated based at least on said page coordinates of said input fields and said page coordinates of said text.

16. The method of claim 1, wherein at least one input element of said plurality of input elements represents a checkbox for receiving a user checkmark.

17. The method of claim 1, wherein at least one input element of said plurality of input elements represents a textbox for receiving user text.

18. A computing device for processing a completed fillable form, said computer device comprising:
 a processor;
 memory in communication with said processor; and
 software code stored in said memory, executable on said processor, said software code comprising:
  a receiving module to receive a parsable electronic representation of said completed finable form, said electronic representation comprising:
   a plurality of input elements, each of said plurality of input elements representing an input field in said completed fillable form, said input field for receiving user-filled data;
   a plurality text elements, each of said plurality of text elements representing text in said completed fillable form, said text providing descriptive context to an input field;
   a plurality of of data elements, each of said plurality of data elements representing user-filled data previously received from a user as input to an input field in said completed fillable form during completion of said fillable form by said user;
  a parsing module to parse said electronic representation;
  an identifying module to identify at least one subset of input elements of said plurality of input elements among:
   a first subset of input elements of said plurality of input elements, said first subset of input elements representing input fields that have received user-filled data represented by said plurality of data elements; or
   a second subset of input elements of said plurality of input elements, said second subset of input elements representing input fields that have not received user-filled data;
  an associating module to determine one or more groupings, each of said groupings associating at least one input element of said at least one subset of input elements with text elements of said plurality of text elements representing text providing descriptive context to input fields represented by said at least one input element;
  a generating module to generate a graphical representation of said completed finable form based on said plurality of input elements, said plurality of text elements and said plurality of data elements, wherein regions of said graphical representation corresponding to said one or more groupings are altered so as to improve visibility of portions of said graphical representation associated with said first subset of input elements relative to portions of said graphical representation associated with said second subset of input elements.

19. A non-transitory computer readable storage medium storing instructions thereon that, when executed by a computer, cause said computer to perform the method of claim 1.

* * * * *